United States Patent
Tanaka et al.

(10) Patent No.: US 6,951,601 B1
(45) Date of Patent: *Oct. 4, 2005

(54) OXYGEN CONCENTRATION DETECTOR

(75) Inventors: Akio Tanaka, Obu (JP); Naoto Miwa, Tsushima (JP); Toshitaka Saito, Toyohashi (JP); Hiromi Sano, Nagoya (JP); Kazunori Suzuki, Nagoya (JP); Masaya Fujimoto, Kariya (JP)

(73) Assignee: Denso Corporation (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 1109 days.

(21) Appl. No.: 08/838,910

(22) Filed: Apr. 11, 1997

Related U.S. Application Data

(63) Continuation of application No. 08/522,085, filed on Aug. 31, 1995, now abandoned.

(30) Foreign Application Priority Data

| Sep. 1, 1994 | (JP) | ............................................. 6-234387 |
| Dec. 28, 1994 | (JP) | ............................................. 6-340136 |

(51) Int. Cl.$^7$ ......................................... G01N 27/409
(52) U.S. Cl. ...................... 204/424; 204/429; 204/408
(58) Field of Search .............................. 204/421–429, 204/408; 205/783.5, 784, 784.5, 785

(56) References Cited

U.S. PATENT DOCUMENTS

| 3,978,006 | A | * | 8/1976 | Topp et al. ................. 204/429 |
| 4,021,326 | A | * | 5/1977 | Pollner et al. .............. 204/429 |
| 4,049,524 | A | * | 9/1977 | Togawa et al. ............. 204/427 |
| 4,096,048 | A | * | 6/1978 | Matsumoto et al. ........ 204/424 |
| 4,174,258 | A | * | 11/1979 | Bode ........................... 204/424 |
| 4,212,720 | A | * | 7/1980 | Maurer et al. .............. 204/428 |
| 4,437,971 | A | * | 3/1984 | Csanitz et al. ............. 204/424 |
| 4,452,687 | A | * | 6/1984 | Torisu et al. ............... 204/427 |
| 4,540,479 | A | * | 9/1985 | Sakurai et al. ............. 204/427 |
| 4,582,657 | A | * | 4/1986 | Shibata et al. ............. 264/40.6 |
| 4,900,412 | A | * | 2/1990 | Ker et al. ................... 204/408 |
| 4,935,118 | A | * | 6/1990 | Agarwal et al. ........... 204/424 |

FOREIGN PATENT DOCUMENTS

| EP | 0 294 085 | 7/1988 |
| JP | 57-142555 | 9/1982 |
| JP | 57178152 | 11/1982 |
| JP | 1-77946 | 5/1989 |
| JP | 2-287251 | 11/1990 |
| JP | 4-124456 | 11/1992 |
| JP | 4-370689 | 12/1992 |
| JP | 5-27660 | 4/1993 |
| JP | 5-126789 | 5/1993 |
| JP | 5-133931 | 5/1993 |
| JP | 6-235713 | 8/1994 |

OTHER PUBLICATIONS

Hackh's Chemical Dictionary, 4th ed. (1969), p. 529.*

* cited by examiner

Primary Examiner—Kaj K. Olsen
(74) Attorney, Agent, or Firm—Nixon & Vanderhye PC

(57) ABSTRACT

The oxygen concentration detector of the present invention includes a sensor element having a solid electrolyte and having an external electrode and an internal electrode provided on the external surface and the internal surface, respectively, and a heater provided adjacent to the internal surface of the sensor element, in which a high-emissivity layer consisting of a material having a high emissivity is provided on the internal surface of the sensor element and/or the surface of the heater.

20 Claims, 12 Drawing Sheets

AIR-FUEL RATIO (A/F)

OXYGEN CONCENTRATION DETECTOR

This is a continuation of application Ser. No. 08/522,085, filed on Aug. 31, 1995, now abandoned, which was abandoned upon the filing hereof.

This application is based upon and claims priority from Japanese Patent Application No. 6-234387 filed Sep. 1, 1994 and Japanese Patent Application No. 6-340136 filed Dec. 28, 1994, with the contents of each document being incorporated herein by reference.

BACKGROUND OF THE INVENTION

1. Field of the Invention

The present invention relates to an oxygen concentration detector having a built-in heater, such as a limiting current type oxygen concentration detector.

2. Description of the Prior Art

Conventionally, in an oxygen concentration detector, a heater is built in an inside of the detector having a solid electrolyte to heat the solid electrolyte and the characterisity of the detector is quickly stabilized. However, recently quicker heating of the solid electrolyte is required.

To achieve the above requirement, one method is to flow a large current to the heater, and the other method is to utilize heat from the heater effectively. However, if a large current is applied, the heater is damaged by an abrupt temperature rise. Therefore, to utilize heat from the heater effectively is thought to be an effective method in the present invention.

SUMMARY OF THE INVENTION

An object of the present invention is to provide an oxygen concentration detector for utilizing heat from the heater effectively.

An oxygen concentration detector of one preferred mode of the present invention includes a sensor element, a heater, and a high-emissivity layer.

The sensor element includes a solid electrolyte and external and internal electrodes provided on external and internal surfaces thereof, respectively. The heater provided adjacent to the internal surface of the sensor element. The high-emissivity layer formed by a material having a high emissivity is provided on at least one of the internal surface of the sensor element and the surface of the heater. In case that the high-emissivity layer is provided on the internal surface of the sensor element, the high-emissivity layer has an emissivity of 0.3 or more. In case that the high-emissivity layer is provided on the surface of said heater, the high-emissivity layer has the emissivity of 0.6 or more. The emissivity is measured within a wavelength of 2–20 $\mu$m at 500° C.

Preferably, the high-emissivity layer provided on the internal surface of the sensor element consists of one or more materials selected from a group consisting of alumina, titanium oxide, zirconium oxide, iron (III) oxide, nickel oxide, manganese oxide, copper oxide, cobalt oxide, chromium oxide, yttrium oxide, cordierite, silicon nitride, aluminum nitride, and silicon carbide.

Preferably, the high-emissivity layer provided on the surface of the heater consists of one or more materials selected from a group consisting of iron (III) oxide, nickel oxide, manganese oxide, copper oxide, cobalt oxide, chromium oxide, silicon nitride, aluminum nitride, and silicon carbide.

It is also preferred that the above high-emissivity layer is porous in order to lead air to the electrode when formed in the sensor element, and that the porosity thereof is 10 percent or more. More preferably, the porosity is 50 percent or more.

Preferably, a surface roughness of the high-emissivity layer is 1 $\mu$m or more. The surface roughness is measured by 10 point mean roughness measurement as defined in Japanese Industrial Standard (JIS) B 0601, incorporated herein by reference. The roughness stated hereinafter is based on the above defined measurement.

It is preferred that the thickness of the high-emissivity layer is 5 microns or more. If the thickness is less than 5 microns, the effect of the high-emissivity layer may be reduced. More preferably, the thickness is 10 to 20 microns. If the thickness exceeds 20 microns, the problem of film pealing off may arise due to decrease in the adhesive force of the film.

Preferably, the heater has a polygonal cross-section.

In the oxygen concentration detector of the present invention, the high-emissivity layer is provided on the internal surface of the sensor element and/or the surface of the heater. This high-emissivity layer is formed by a material having a high emissivity.

When the high-emissivity layer is provided on the internal surface of the sensor element, the high-emissivity layer absorbs heat radiated from the heater efficiently, and heats the solid electrolyte sufficiently.

When the high-emissivity layer is formed on the surface of the heater, the high-emissivity layer absorbs heat from the heater efficiently, and radiates it to the internal surface of the sensor element efficiently. When the high-emissivity layers are provided both on the internal surface of the sensor element and on the surface of the heater, a synergistic effect is obtained.

According to the present invention, therefore, heat from the heater is efficiently transferred to the sensor element, and the sensor element is efficiently heated. Even if the temperature of the gas to be measured is low, it is not required to elevate the temperature of the heating element of the heater extremely. Therefore, the durability of the heater is improved.

Also, since the sensor element is efficiently heated, the temperature of the sensor element may be elevated even when the temperature of the gas to be measured is low, such as engine exhaust gas, and stable sensor properties are exerted.

According to the present invention, therefore, an oxygen concentration detector having the heater with an improved durability, and exerting stable sensor properties even at low temperatures is provided.

DETAILED DESCRIPTION OF THE PREFERRED EMBODIMENTS

Embodiment 1

An oxygen concentration detector according to an embodiment of the present invention, a method for the manufacture thereof, and the evaluation of the oxygen concentration detector will be described referring to FIGS. 1 to 4.

Figure 1:
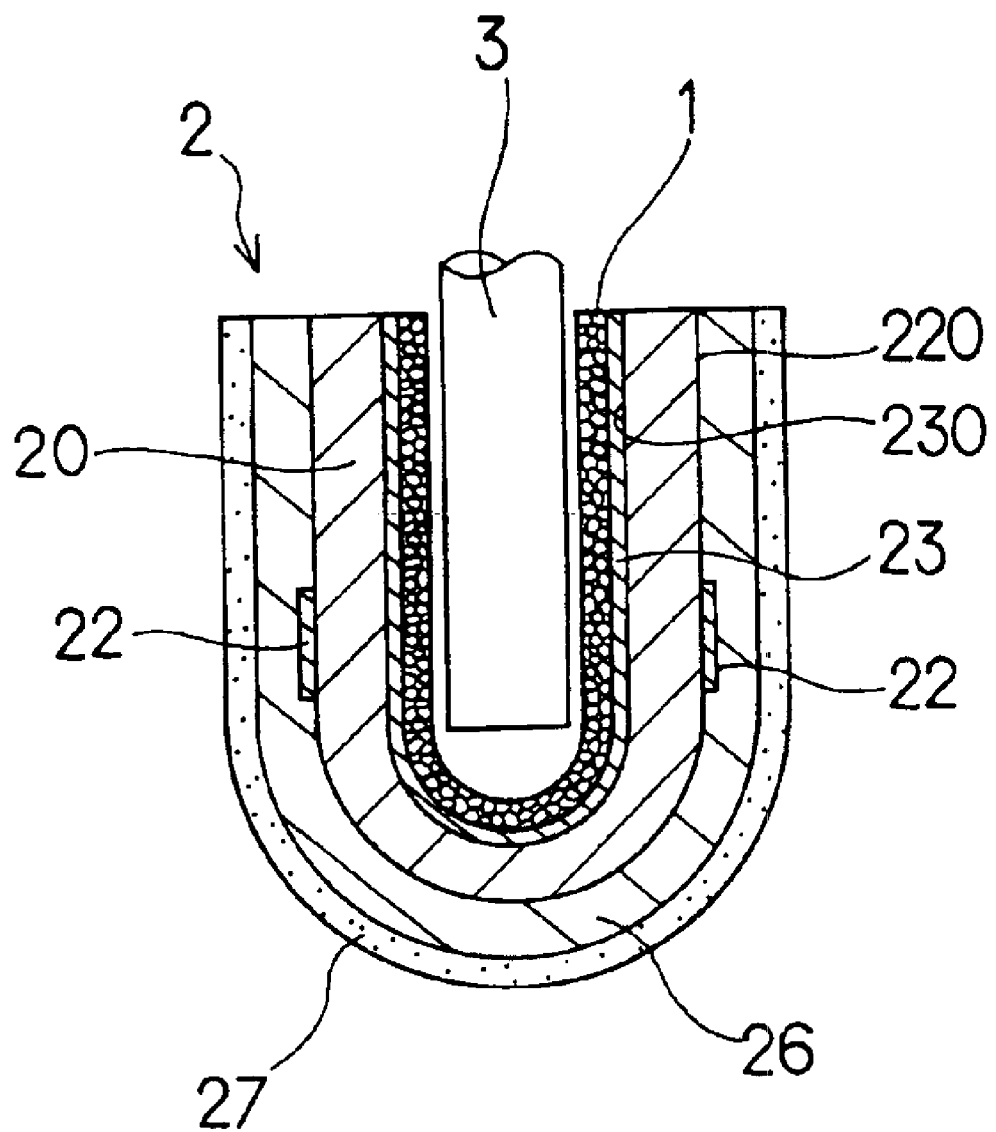
FIG. 1 is a partially schematic sectional view illustrating the oxygen concentration detector of Example 1.
Figure 2:
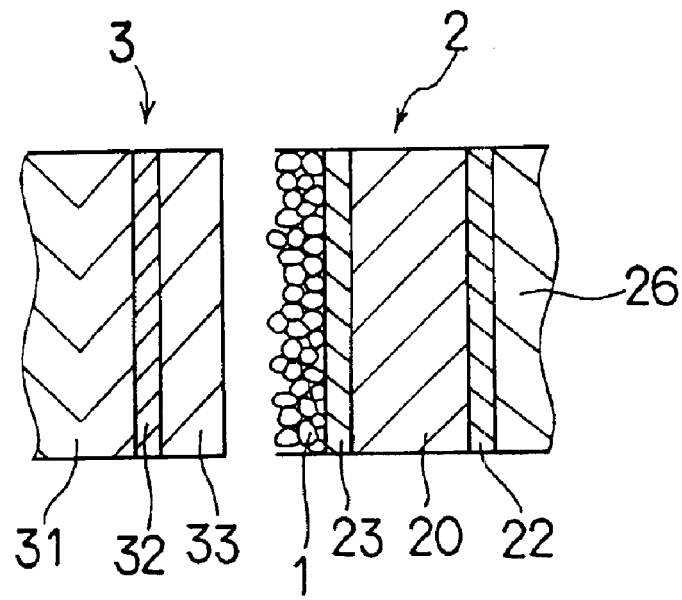
FIG. 2 is an enlarged view illustrating the part of the sensor element facing to the heater in the oxygen concentration detector of Example 1.
Figure 4:
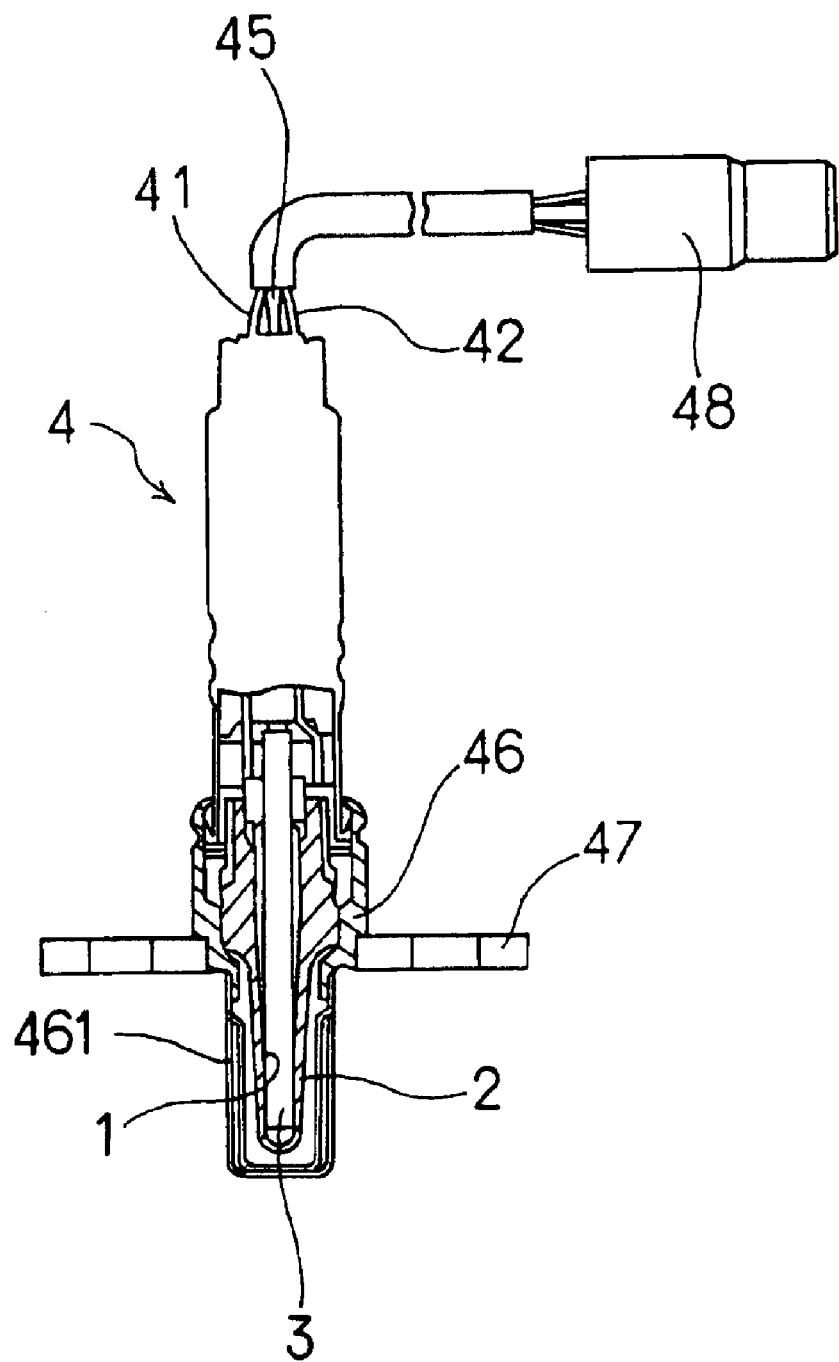
FIG. 4 is a general schematic view illustrating the oxygen concentration detector of Example 1.

As FIGS. 1, 2, and 4 show, the oxygen concentration detector of this embodiment comprises a sensor element 2 consisting of a solid electrolyte 20, and provided with an external electrode 22 and an internal electrode 23 formed on the external surface 220 and the internal surface 230 of the sensor element, respectively, and a heater 3 installed adjacent to the internal surface 230 of the sensor element.

The above heater is composed of one or more highly heat resistant and high-emissivity materials selected from a group consisting of silicon nitride, aluminum nitride and silicon carbide.

The internal surface 230 of the sensor element 2 is provided with a high-emissivity layer 1 formed by a material having a high emissivity.

The oxygen concentration detector 4 (FIG. 4) of this embodiment is a limiting current type oxygen concentration detector for the measurement of engine exhaust gas as described later.

As FIGS. 1 and 2 show, the sensor element 2 is cup-shaped and consists of zirconia solid electrolyte 20, of which the internal surface 230 has an internal electrode 23 contacting the air, and the external surface 220 has a cylindrical external electrode 22 contacting the engine exhaust gas as the gas to be measured. These internal. electrode 23 and external electrode 22 have platinum layers formed, for example, by electroless plating.

A porous high-emissivity layer according to the present invention is formed on the internal surface 230 so as to cover the internal electrode 23.

A gas diffusion layer 26 is formed on the external surface of the solid electrolyte 20 so as to cover the external electrode 22, and a porous trap layer 27 is formed on the further external surface. The gas diffusion layer 26 is a plasma-coated porous alumina-magnesia layer. The trap layer 27 is formed for protecting the sensor element 2 by trapping poisonous substances such as phosphorus (P) and lead (Pb) in exhaust gas, and consists of alumina.

Figure 20:
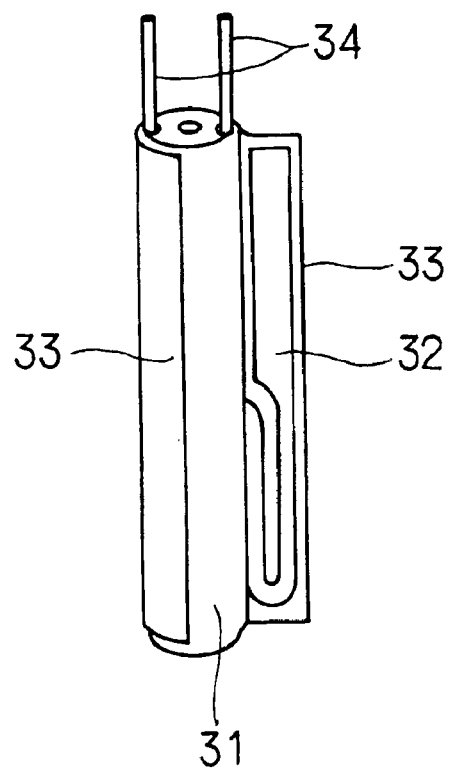
FIG. 20 is a perspective view showing the heater during the sheet winding in a conventional example.

On the other hand, as FIGS. 1, 2 and 20 show, the heater 3 has a heating element 32 of platinum or tungsten provided on the surface of a ceramic rod 31 such as alumina, and is coated with an alumina sheet 33. This heating element 32 has previously been printed on the sheet 33, and is formed by winding together with the sheet 33 around the ceramic rod 31. The symbolic numeral 34 indicates lead wires.

The porous high-emissivity layer 1 was formed by preparing a slurry of a high-emissivity material powder described later dispersed in water, applying it to the internal surface 230 of the sensor element 2, drying it, and baking it by heating the sensor element at about 1000° C. The slurry was applied by pouring the slurry on to the cup-shaped internal surface 230 of the sensor element, then removing the excessive slurry.

The surface roughness of the internal surface 230 was about 10 $\mu$m.

The porosity of the high-emissivity layer 1 is set at 50 percent in this embodiment by considering the diffusion of the air inside the sensor element.

Next, the oxygen concentration detector 4 after installing the sensor element 2 and the heater 3 will be described referring to FIG. 4.

The oxygen concentration detector 4 comprises a sensor element 2 in which a heater 3 is inserted, and is covered with a housing 46 and a case 461 having a window. The external electrode 22, the internal electrode 23, and the heater 3 are connected to a connector 48 on the upper part of the sensor element via lead wires 41, 42, and 45, respectively. The oxygen concentration detector 4 thus constructed is fixed on the engine exhaust pipe by a flange 47 installed on the housing 46.

Figure 3:
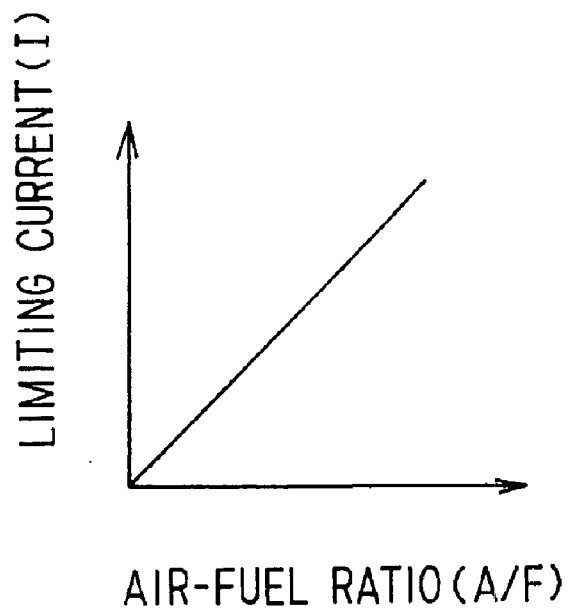
FIG. 3 is a graph showing the relationship between air-fuel ratio and the limiting current of the limiting current type oxygen concentration detector of Example 1.

This oxygen concentration detector 4 is of a limiting current type, in which oxygen ions are diffused in the solid electrolyte by applying a voltage between the external electrode 22 and the internal electrode 23, and the limiting current value for the concentration of diffused oxygen ions is measured. FIG. 3 shows relationship between the air/fuel ratio (A/F=amount of air/amount of fuel) of the engine and the limiting current value when engine exhaust gas is measured using this oxygen concentration detector.

Embodiment 2

Next, the oxygen concentration detector of Embodiment 1 in which a high-emissivity layer was formed only on the internal surface of the sensor element (Table 1) was evaluated.

The area of the high-emissivity layer formed on the internal surface of the sensor element was 60 percent of the area of the internal surface, and the thickness of the high-emissivity layer was about 20 $\mu$m. The type of the high-emissivity layers, and the emissivity at 500–1200° C. are shown in Table 1.

The oxygen concentration detector was evaluated how high the temperature of the solid electrolyte in the sensor element rose when the temperature of the heater was maintained at 1050° C. Actually, the evaluation was performed under the condition where a power of 28 W(watts) was applied to the heater.

The oxygen concentration detector was placed in engine exhaust gas, and the performance of the sensor during engine idling was measured. The internal resistance of the sensor element during idling was evaluated in three ranks of 20 k$\Omega$(kiloohms) or below, 20–40 k$\Omega$, and 40 k$\Omega$ or above.

The results are shown in Table 1.

As comparative examples, the same measurement was conducted on conventional detectors having Pt-plated and Au-plated electrodes without providing high-emissivity layers (Sample Nos. C1 and C2).

Results for these examples are also shown in Table 1.

As Table 1 shows, since the oxygen concentration detectors according to the present invention (Sample Nos. 1–6) have high-emissivity layers formed on the internal surfaces of sensor elements, the solid electrolyte shows a high temperature, making the oxygen concentration detectors exert excellent sensor properties. This is because the high-emissivity layers have emissivity as high as 0.3 or more. On the other hand, in comparative examples C1 and C2, the temperature of the solid electrolyte is low, and the sensor properties are poor. This is because the emissivities of Pt plating of comparative example C1 and Au plating of comparative example C2 are as low as 0.1 and 0.03, respectively.

TABLE 1

Examples having high-emissivity layers on the internal surfaces of sensor elements

| Sample No. | High-emissivity layer | Emissivity | Solid electrolyte temperature | Sensor #1 properties |
|---|---|---|---|---|
| Present invention | | | | |
| 1 | $Al_2O_3$ film | 0.3 | 680° C. | o |
| 2 | $ZrO_2$ film | 0.4 | 690° C. | o |
| 3 | $Fe_2O_2$ film | 0.7 | 695° C. | o |
| 4 | NiO film | 0.9 | 700° C. | o |
| 5 | $Al_2O_3$, $Fe_2O_3$, CoO, $Mn_2O_3$ film | 0.9 | 700° C. | o |
| 6 | CuO, $Fe_2O_3$, $Mn_2O_3$ film | 0.8 | 700° C. | o |
| Comparative example | | | | |
| C1 | None (Pt) | 0.1 | 650° C. | $\Delta$ |
| C2 | None (Au) | 0.03 | 640° C. | x |

\* Criterions for sensor properties: The internal resistance of the sensor element during idling
1: o: 20 kQ or less; $\Delta$: 20–40 kQ, x: 40 kQ or more Embodiment 3

Figure 5:
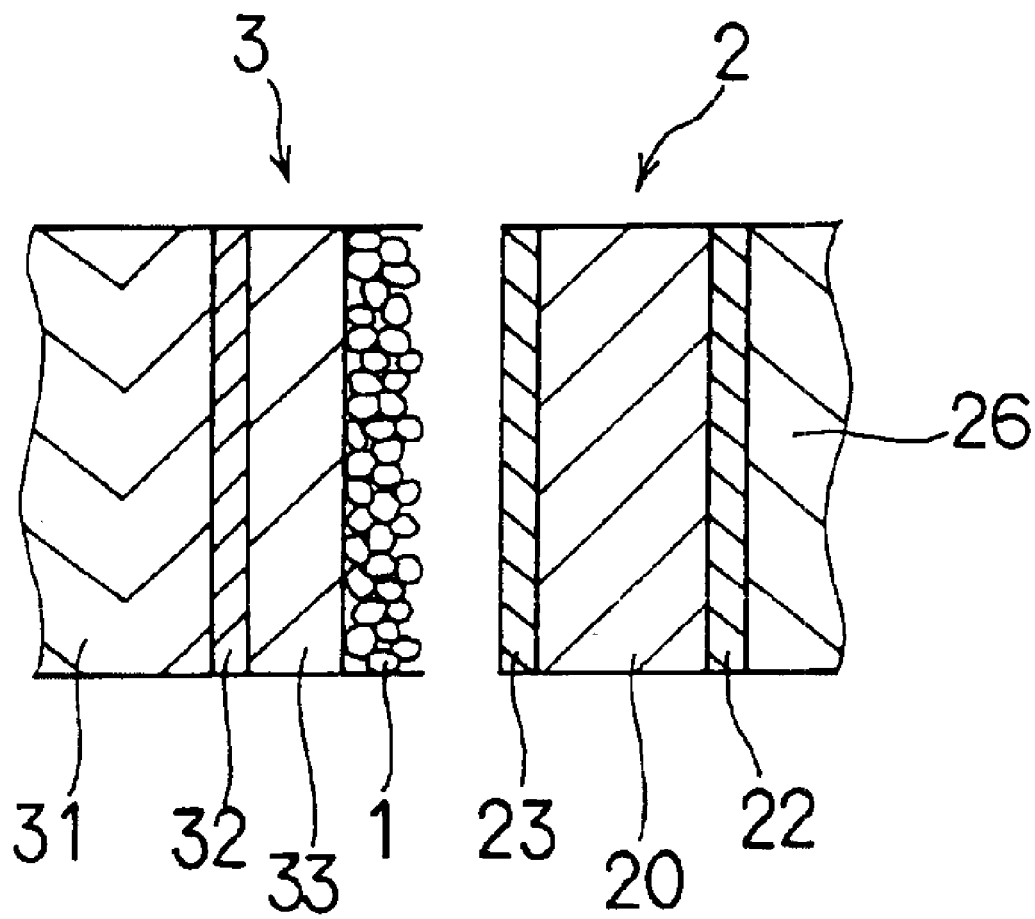
FIG. 5 is an enlarged view illustrating the part of the sensor element facing to the heater in the oxygen concentration detector of Example 3.
Figure 6:
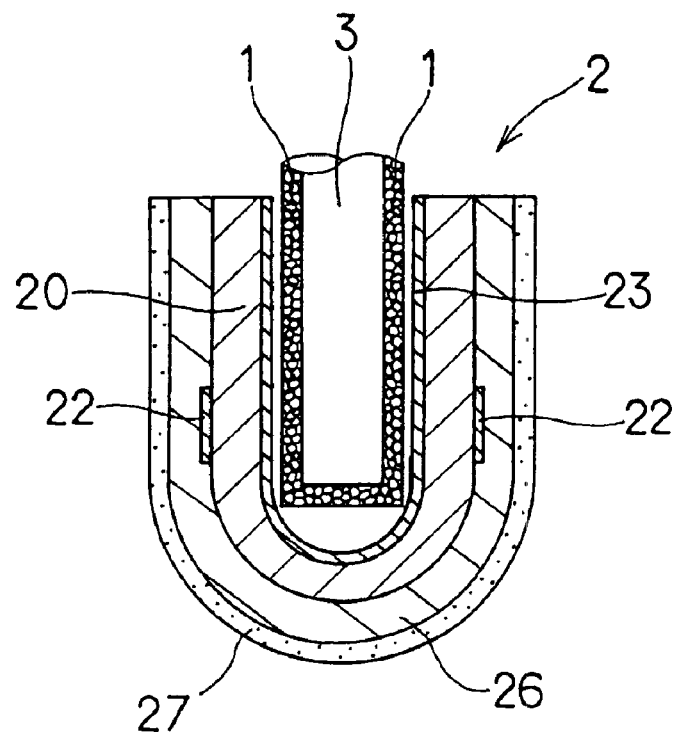
FIG. 6 is a partially schematic sectional view illustrating the oxygen concentration detector of Example 3.

The oxygen concentration detector of this embodiment is, as FIGS. 5 and 6 show, an embodiment in which a high-emissivity layer is formed on the surface of the heater.

The oxygen concentration detector of this embodiment comprises a heater 3 having a heating element 32 coated with an alumina sheet 33, and further coated with a high-emissivity layer 1 according to the present invention. No high-emissivity layer is formed on the sensor element 2 side. Other aspects are the same as Embodiment 1.

In the case of this embodiment, three types of high-emissivity layers (Sample Nos. 7–9) were used as Table 2 shows. The high-emissivity layers 1 were formed, as FIGS. 5 and 6 show, on the surface of the alumina sheet 33 which covers the heating element 32 of the heater. The thickness of the high-emissivity layers was 20 $\mu$m. The high-emissivity layers 1 were formed by immersing the heater in the slurry of a high-emissivity material ($Y_2O_3$, $Fe_2O_3$ or NiO in Table 2), drying and baking.

As a comparative example, the heater only coated with an alumina sheet 32 without providing the high-emissivity layer 1 as in conventional practice was used.

The oxygen concentration detectors of this embodiment were evaluated in the same way as in Embodiment 2. The results are shown in Table 2.

It is seen from Table 2 that the oxygen concentration detectors of the present invention (Sample Nos. 7–9) show a high solid electrolyte temperature even when a high-emissivity layer is formed on the heater, and exert an excellent sensor properties. In Comparative Example C3, on the other hand, although an alumina sheet is provided on the outermost surface of the heater 3, the temperature of the solid electrolyte is low because the emissivity of the alumina sheet is low.

As is known from the above description, according to the present invention, the durability of the heater is improved, and the oxygen concentration detector exerting stable sensor properties is obtained.

TABLE 2

Examples having high-emissivity layers on the surfaces of heaters

| Sample No. | High-emissivity layer | Emissivity | Solid electrolyte temperature | Sensor properties |
|---|---|---|---|---|
| Present invention | | | | |
| 5 | $Y_2O_3$ film | 0.6 | 670° C. | o |
| 6 | $Fe_2O_3$ film | 0.7 | 675° C. | o |
| 7 | NiO film | 0.9 | 680° C. | o |
| Comparative example | | | | |
| C3 | None ($Al_2O_3$ sheet) | 0.3 | 650° C. | $\Delta$ |

Embodiment 4

Although the above embodiments 1–3 are oxygen concentration detectors of the limiting current type, this embodiment is an oxygen concentration detector of the electromotive force type.

Figure 7:
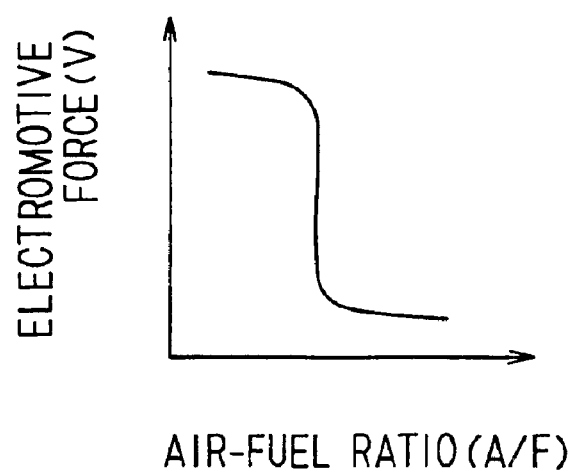
FIG. 7 is a graph showing the relationship between the air-fuel ratio and the electromotive force of the oxygen concentration detector of Example 4.

As FIG. 7 shows, this type of the oxygen concentration detectors have characteristics in which the electromotive force changes suddenly at an air-to-fuel ratio.

Embodiment 5

In the oxygen concentration detector shown in the above embodiments, when the air side electrode (internal surface of the sensor element) is formed by the paste of platinum and the like, a high-emissivity heat-resistant metal oxide, such as alumina, zirconium oxide, iron (III) oxide, and nickel oxide, is mixed with the material for the electrode such as platinum to form a paste electrode to make the emissivity of the electrode itself 0.3 or more.

By thus integrating the electrode and the high-emissivity layer, the effect as same as in Embodiment 1 is also obtained.

Embodiment 6

Figure 8:
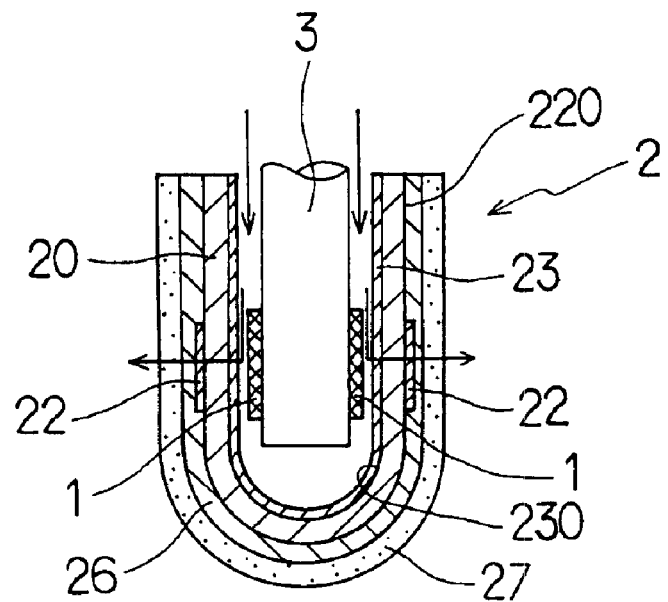
FIG. 8 is a partially schematic sectional view illustrating the oxygen concentration detector of Example 6.

This embodiment is similar to the oxygen concentration detector of Embodiment 3, in which a high-emissivity layer 1 is partially formed on the surface of the heater 3 as FIG. 8 shows.

In the sensor element 2, the external electrode 22 is provided on the lower end of the side of the solid electrolyte 20 as a band. On the other hand, the high-emissivity layer 1 is also provided on the lower end of the side of the heater 3, which is the location facing to the external electrode 22, as a band. On the upper part of the heater 3, no high-emissivity layer 1 is provided. Otherwise, this embodiment is the same as Embodiment 1.

In an oxygen concentration detector used for the control of air-fuel ratios of engine, when the air-fuel ratio is rich, oxygen supplied from the clearance between the heater 3 and the internal electrode 23 becomes oxygen ions in the internal electrode 23, which move to the external electrode 22 through the solid electrolyte 20, as the arrow in FIG. 8 shows. By this phenomenon, the oxygen concentration detector detects that the air-fuel ratio is rich. If the inside of the sensor element 2 were under the condition of oxygen depletion, the correct detection of the air-fuel ratio could not be achieved.

The oxygen concentration detector of this embodiment has the structure in which the clearance between the internal electrode 23 and the heater 3 is wide at the upper part of the heater 3, and oxygen flows in easily. Therefore, the oxygen depletion in the sensor element 2 is prevented, and the air-fuel ratio is measured accurately. In addition to this, the same effect as in Embodiment 1 is obtained.

It is preferred that the clearance between the high-emissivity layer 1 and the internal electrode 23 is 0.1 mm or more so as not to interfere with the movement of oxygen and the like.

Embodiment 7

Figure 9:
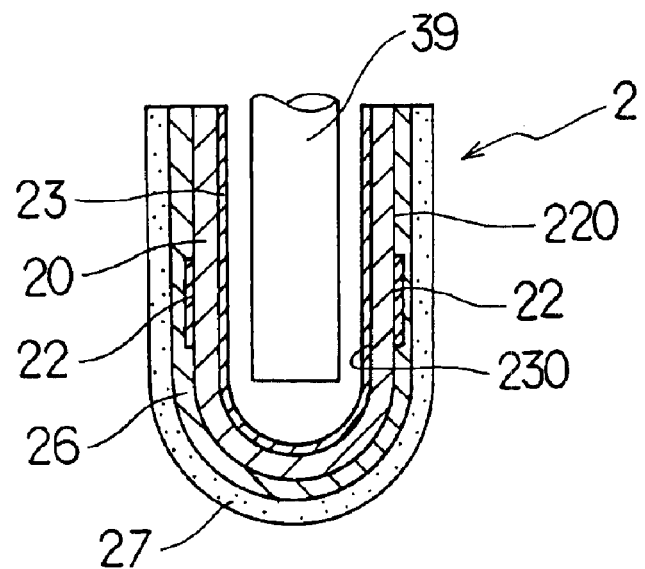
FIG. 9 is a partially schematic sectional view illustrating the oxygen concentration detector of Example 7.

As FIGS. 9 and 10 show, the oxygen concentration detector of this embodiment has a heater 39 consisting of silicon nitride which has high heat resistance and high emissivity.

Figure 10A:
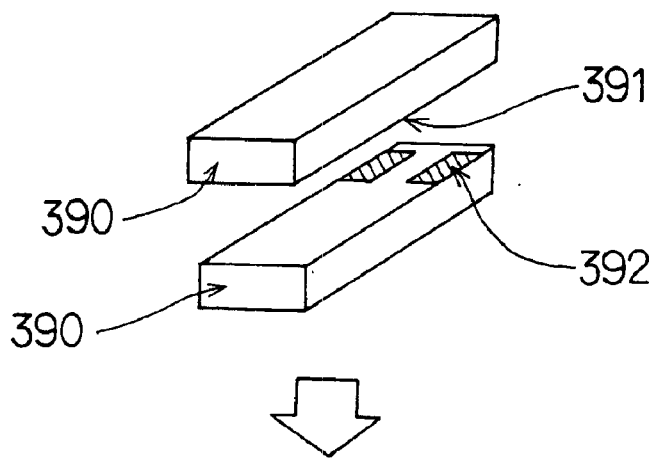
FIGS. 10A to 10C are views for illustrating the manufacturing steps of the heater for the oxygen concentration detector of Example 7.

As is shown in FIG. 10A, in the formation of the heater 39, two moldings of the same shape 390 consisting of silicon nitride are provided. One of the moldings 390 is printed with a W—Mo (tungstein-molybdenum) conductor paste 392 at two locations, and a tungstein wire 391 is connected to the other molding 390. The tungstein wire 391 and the conductor paste 392 may be provided on the same molding.

Next, while making the conductor paste 392 to face to the tungsten wire 391, the both moldings 390 are laminated to form a laminate. Then, the laminate is sintered in the hot press at a temperature between 1700 and 1800° C. to form a sintered article.

Figure 10B:
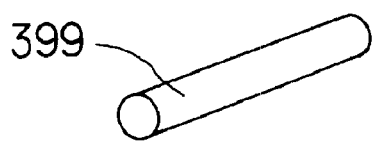
Figure 10C:
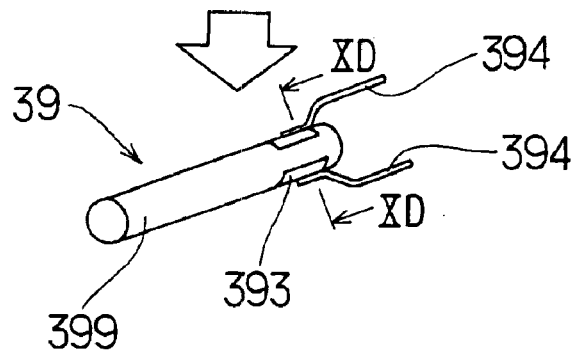
Figure 10D:
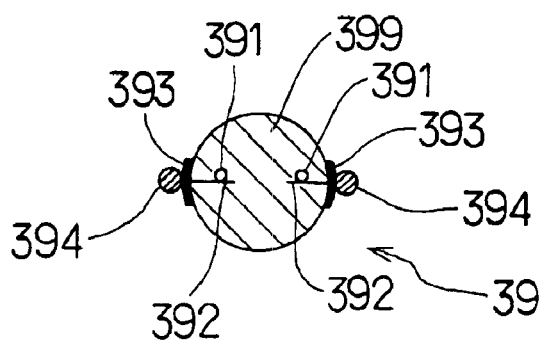
FIG. 10D is a sectional view taken along the line XD—XD in FIG. 10C.

Next, as FIG. 10B shows, the sintered article is machined to be a cylindrical article 399. Then, as FIG. 10C shows, two Ni lead wires 394 are brazed on to the side of the cylindrical article 399 using an Au—Ni braze 393 for making conduction with the conductor paste 392. That is, as FIG. 10D shows, since the conductor paste 392 is exposed on the side of the cylindrical article 399, the Au—Ni braze 393 is provided to cover the conductor paste 392. By this, the heater 39 consisting of silicon nitride is obtained.

This heater 39 is inserted into the sensor element 2 as FIG. 9 shows. Other steps are the same as in Embodiment 1.

In the oxygen concentration detector of this embodiment, since the heater 39 consists of a material having a high heat resistance and a high emissivity, the sensor element 2 is efficiently heated. In addition to this, the same effect as in Embodiment 1 is obtained.

Embodiment 8

Figure 11:
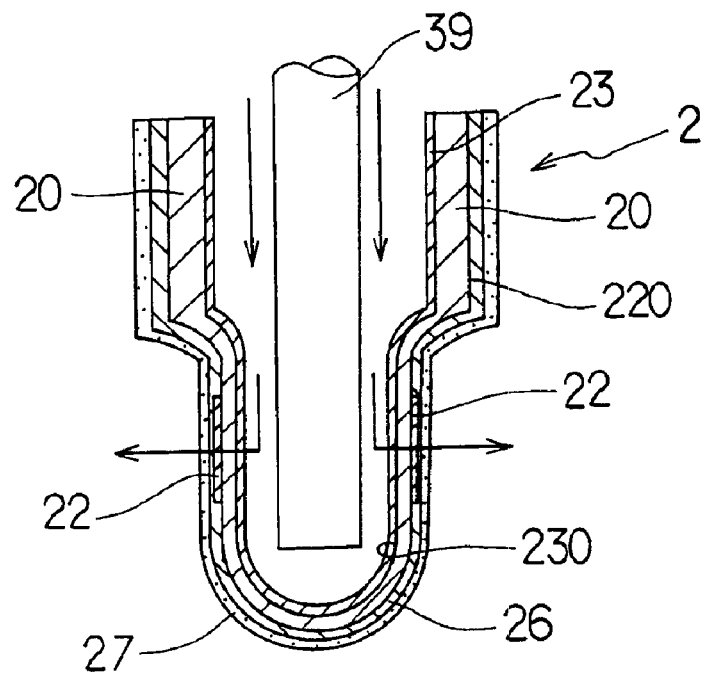
FIG. 11 is a partially schematic sectional view illustrating the oxygen concentration detector of Example 8.

As FIG. 11 shows, the oxygen concentration detector of this embodiment has a sensor element 2 constituted so that the clearance between the internal electrode 23 and the heater 39 at the upper part of the sensor element 2 is wider, and the clearance between the internal electrode 23 and the heater 39 in the vicinity of the external electrode 22 is narrower.

The heater 39 inserted into the sensor element 2 is the heater 39 consisting of a material having a high heat resistance and a high emissivity as in Embodiment 7. Other steps are the same as in Embodiment 1.

In the oxygen concentration detector of this embodiment, since the clearance between the internal electrode 23 and the heater 39 is wide at the upper part of the heater 39, oxygen flows in easily. Therefore, oxygen depletion in the sensor element 2 is prevented, and the air-to-fuel ratio is accurately measured. In addition to this, the same effect as in Embodiment 1 is obtained.

The clearance between the heater 39 and the internal electrode 23 is preferably 0.1 mm or more so as not to interfere with the movement of oxygen and the like.

Embodiment 9

Figure 12:
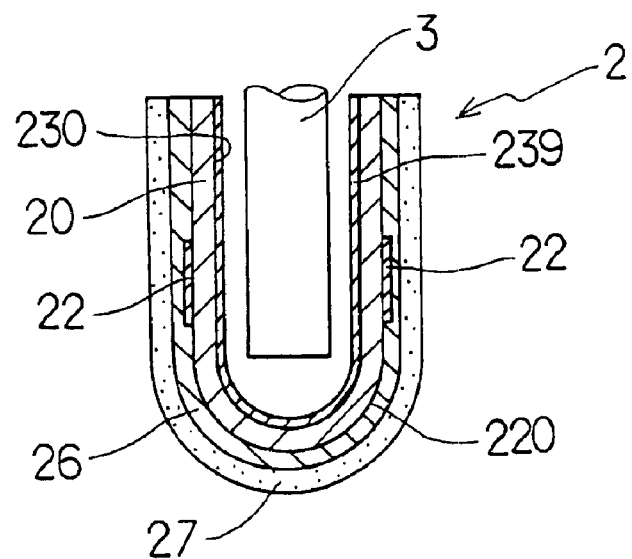
FIG. 12 is a partially schematic sectional view illustrating the oxygen concentration detector of Example 9.

The oxygen concentration detector of this embodiment is an embodiment in which the internal electrode 239 in the sensor element 2 consists of a material having a high emissivity such as platinum black or ruthenium oxide as FIG. 12 shows.

In the formation of the internal electrode 239, in the case of platinum black, the paste is produced by mixing 82 percent by weight of platinum black powder with 18 percent by weight of the mixture of an organic binder and an organic solvent. On the other hand in the case of ruthenium oxide, the paste is produced by mixing 76 percent by weight of ruthenium oxide powder with 24 percent by weight of the mixture of an organic binder and an organic solvent.

Next, the above paste is applied to the surface of the solid electrolyte 20 by curved-surface printing. Then, the solid electrolyte 20 is allowed to stand in the air for 10 minutes for leveling. The solid electrolyte 20 is then placed in a sintering furnace, and sintered at a temperature between 1100 and 1400° C. for 5 hours in the air for platinum black, and at a temperature between 760 and 850° C. for 10 minutes in the air for ruthenium oxide.

By this, the internal electrode 239 is formed on the internal surface 230 of the solid electrolyte 20. Other steps are the same as in Embodiment 1.

In the oxygen concentration detector of this embodiment, the internal electrode 23 consists of a high-emissivity material. Therefore, heat from the heater 3 is efficiently transferred to the sensor element 2, and the sensor element 2 is efficiently heated. In addition to this, the same effect as in Embodiment 1 is obtained.

Embodiment 10

Figure 13:
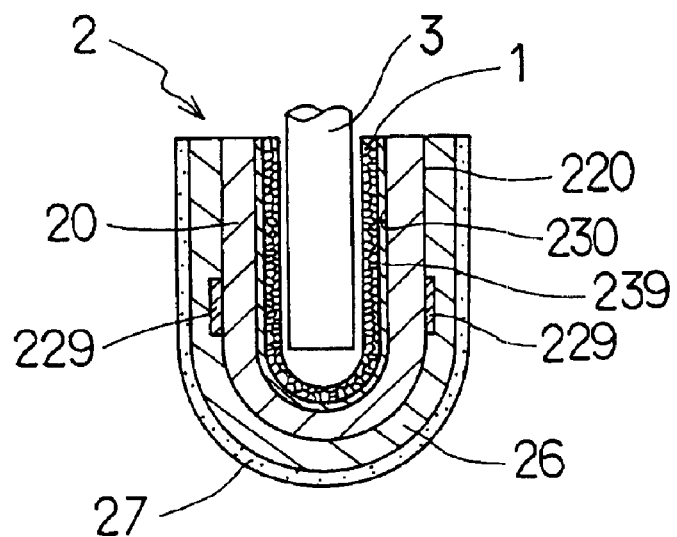
FIG. 13 is a partially schematic sectional view illustrating the oxygen concentration detector of Example 10.

As FIG. 13 shows, the oxygen concentration detector of this embodiment has a high-emissivity layer 1 consisting of a material having a high emissivity formed on the surface of the internal electrode 239, while the external electrode 229 consists of a material having an emissivity lower than the emissivity of the high-emissivity layer 1.

The high-emissivity layer 1 consists of one of the materials shown in Table 2 and the like.

On the other hand, under the condition that the external electrode 229 has an emissivity lower than the emissivity of the high-emissivity layer 1, the external electrode 229 is composed, for embodiment, of platinum (emissivity: 0.1), gold (emissivity: 0.03), or palladium (emissivity: 0.33). Other steps are the same as in Embodiment 1.

In the oxygen concentration detector of this embodiment, since a high-emissivity layer 1 is provided on the internal electrode 23, heat radiated from the heater 3 is efficiently absorbed. On the other hand, since the external electrode 22 consists of a material having a low emissivity, little heat is dissipated out of the sensor element 2. Therefore, the sensor element 2 is efficiently heated. In addition to this, the same effect as in Embodiment 1 is obtained.

Embodiment 11

Figure 14:
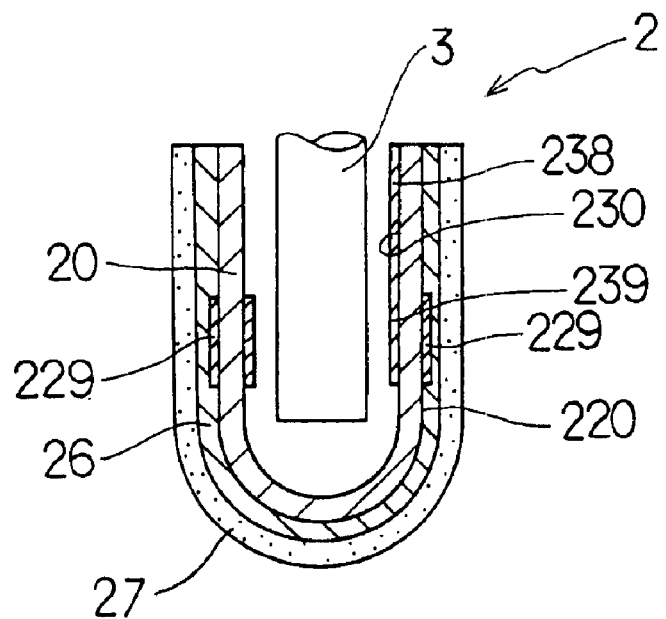
FIG. 14 is a partially schematic sectional view illustrating the oxygen concentration detector of Example 11.

As FIG. 14 shows, the oxygen concentration detector of this embodiment has an internal electrode 239 consisting of a material having an emissivity higher than the emissivity of the external electrode 229 in the location in the sensor element 2 facing to the external electrode 229.

That is, the external electrode 229 is provided on the lower end of the side of the solid electrolyte 20 as a band. On the other hand, the internal electrode 239 is also provided on the lower end of the side of the heater 3 as a band. No internal electrode 239 is provided on the upper part of the sensor element 2.

The internal electrode 239 is composed of platinum black and the like as in Embodiment 9. Also, the external electrode 229 is composed of platinum and the like having a low emissivity as in Embodiment 10. Other steps are the same as in Embodiment 1.

In FIG. 14, the symbolic numeral 238 indicates a lead for conducting the internal electrode 239 with the external terminal (not shown).

The oxygen concentration detector of this embodiment has an internal electrode 239 provided only on the minimum required area. By this, the material costs for forming electrodes are reduced. In addition to this, the same effect as in Embodiment 1 is obtained.

Embodiment 12

Figure 15:
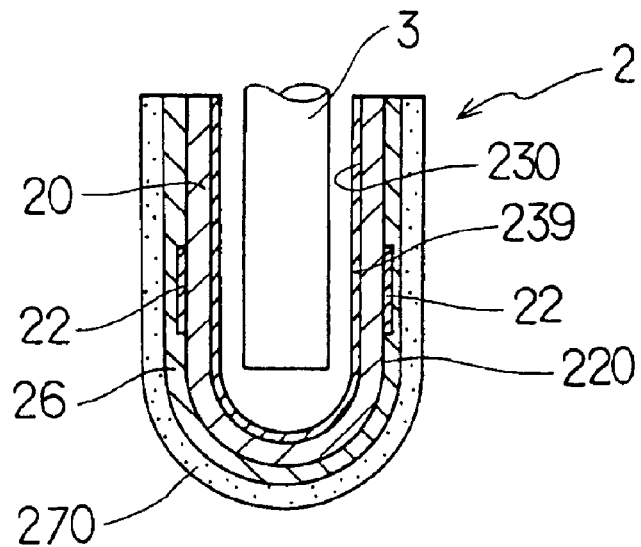
FIG. 15 is a partially schematic sectional view illustrating the oxygen concentration detector of Example 12.

As FIG. 15 shows, the oxygen concentration detector of this embodiment has the outermost layer 270 consisting of a material having an emissivity lower than the emissivity of the internal electrode 239 provided on the sensor element 2.

That is, the outermost layer 270 is provided on the surface of the gas diffusion layer 26 in the sensor element 2, and consists for example of alumina, zirconia or magnesia. The outermost layer 270 is a porous layer easily transmitting the gas to be measured.

The outermost layer 270 is formed by the method to prepare a powdered material consisting of the substances described above, and apply the powdered material by plasma coating, the method to prepare the slurry of the powdered material, and apply and bake this slurry, or the method for vaporizing such as spattering and heat-treating.

On the other hand, the internal electrode 239 is composed of platinum black as in Embodiment 9. Other steps are the same as in Embodiment 1.

Since the oxygen concentration detector of this embodiment has an internal electrode 239 consisting of a material having a high emissivity, heat from the heater 3 is efficiently absorbed. On the other hand, since the outer-most layer 270 of the sensor element 2 consists of a material having a low emissivity, little heat is dissipated out of the sensor element 2. Therefore, the sensor element 2 is efficiently heated. In addition to this, the same effect as in Embodiment 1 is obtained.

Embodiment 13

Figure 16A:
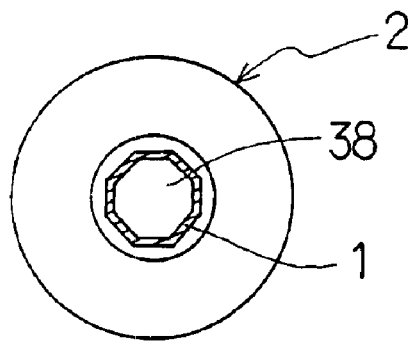
FIG. 16A is a schematic sectional view of the sensor element in the oxygen concentration detector of Example 13.
Figure 16B:
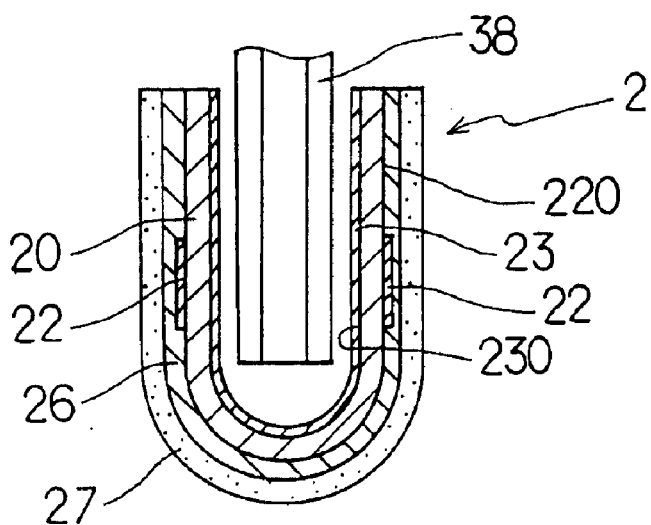
FIG. 16B is a partially schematic sectional view thereof.

As FIGS. 16A and 16B show, the oxygen concentration detector of this embodiment comprises a heater 38 having a polygonal cross-section.

That is, the heater 38 has an octagonal cross-section, and a high-emissivity layer 1 is provided on the surface of the heater 38. Other steps are the same as in Embodiment 1.

Columnar bodies having the same cross-sectional area have a larger surface area when the cross-section is polygonal than circular. Therefore, the heater 38 of this embodiment has a larger surface area, and heats the sensor element 2 more efficiently. In addition to this, the same effect as in Embodiment 1 is obtained.

Embodiment 14

Figure 17:
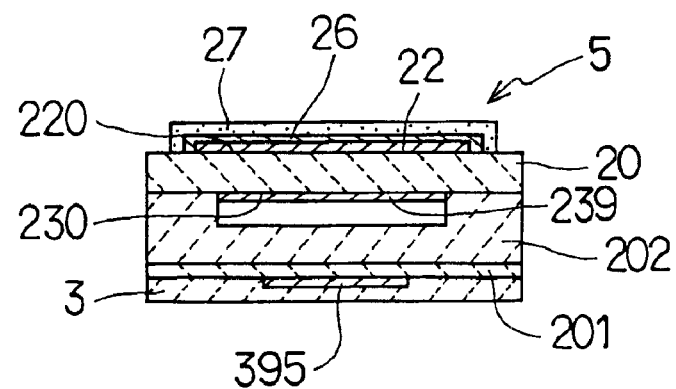
FIG. 17 is a partially schematic sectional view illustrating the sensor element in the oxygen concentration detector of Example 14.
Figure 18:
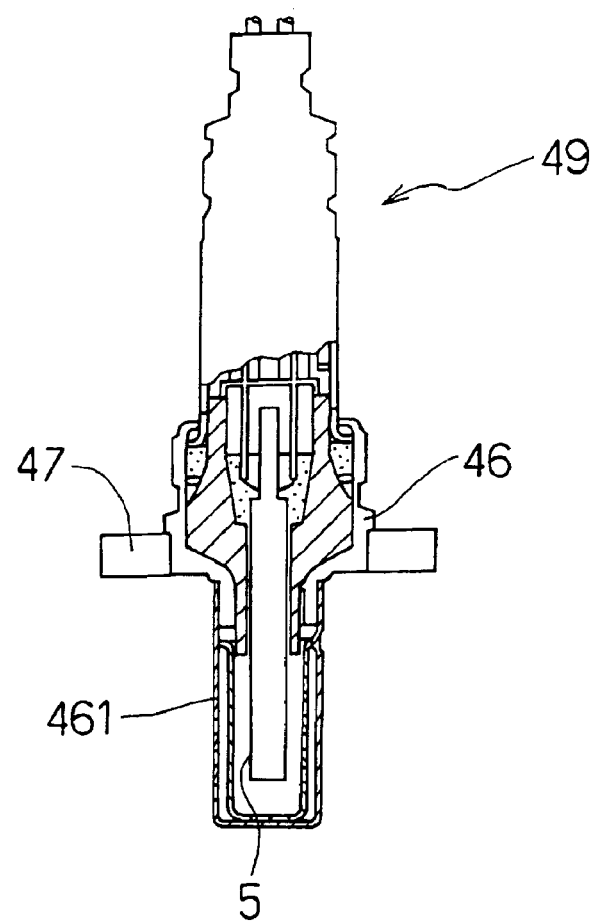
FIG. 18 is a partially schematic sectional view illustrating the oxygen concentration detector of Example 14.

Although the above Embodiments 1–13 are oxygen concentration detectors using cup-shaped sensor elements, this embodiment is an oxygen concentration detector 49 comprising a laminate-type sensor element as FIGS. 17 and 18 show.

The laminate-type sensor element 5 comprises heaters 3 having heating elements 395 formed on the solid electrolyte 20 together with alumina substrates 201 and 202. In the space between the solid electrolyte 20 and the alumina substrate 202, an internal electrode 239 is provided on the internal surface 230 of the solid electrolyte 20. On the other hand, an external electrode 22 is provided on the external surface 220 of the solid electrolyte 20, and a glass diffusion layer 26 and a trap layer 27 are sequentially laminated on the surface of the external electrode 22.

The internal electrode 239 is composed of a material having a high emissivity such as platinum black, as in Embodiment 9.

In forming the internal electrode 239 of this embodiment, the paste as described in Embodiment 9 is provided on the internal surface 230 of the solid electrolyte 20, and in this embodiment, the paste is applied on the surface of the solid electrolyte 20 by screen printing.

As FIG. 18 shows, the oxygen concentration detector 49 of this embodiment is formed by installing a sensor element 2 having a heater 3 in the housing 46. Therefore, no single heater is used unlike the previous embodiments. Other steps are the same as in Embodiment 1.

In the oxygen concentration detector 49 of this embodiment, the internal electrode 23 is composed of a high-emissivity material. Therefore, heat from the heater 3 is efficiently transferred to the sensor element 5, and the sensor element 2 is efficiently heated. In addition to this, the same effect as in Embodiment 1 is obtained.

Embodiment 15

Figure 19:
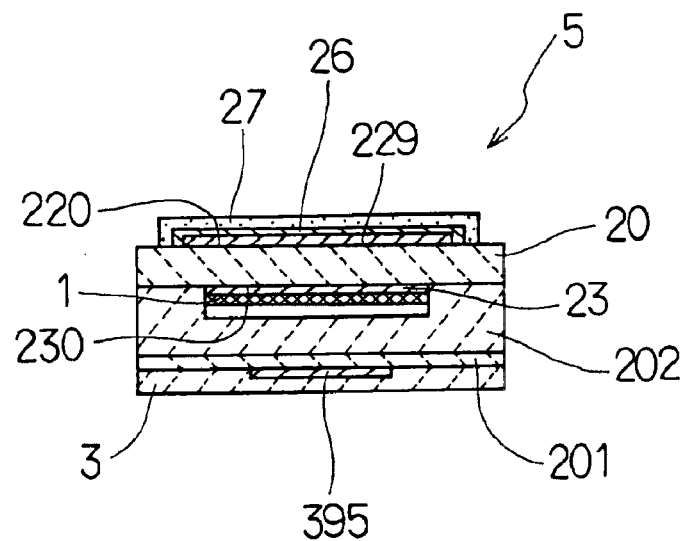
FIG. 19 is a partially schematic sectional view illustrating the sensor element in the oxygen concentration detector of Example 15.

As FIG. 19 shows, the oxygen concentration detector of this embodiment uses a laminate-type sensor element 5 having a high-emissivity layer 1 formed on the surface of the internal electrode 23 as in the cup-shaped sensor element 2 in Embodiment 10.

The high-emissivity layer 1 is composed of one of the materials shown in the above Table 2 and the like.

On the other hand, the external electrode 229 has an emissivity lower than the emissivity of the internal electrode 23, and is composed for embodiment of platinum, gold or palladium. Other steps are the same as in Embodiment 1.

In the oxygen concentration detector of this embodiment, since a high-emissivity layer 1 is provided on the internal electrode 23, heat from the heater 3 is efficiently absorbed. On the other hand, since the external electrode 22 is composed of a material having a low emissivity, little heat is dissipated out of the sensor element 2. Therefore, the heater 3 heats the sensor element 2 efficiently. In addition to this, the same effect as in Embodiment 1 is obtained.

What is claimed is:

1. An oxygen concentration detector comprising:
    a sensor element including a solid electrolyte and external and internal electrodes provided on external and internal surfaces thereof, respectively;
    a heater provided adjacent to said internal surface of said sensor element; wherein said internal electrode consists of a material having an emissivity of 0.3 or more, and said external electrode consists of a material having an emissivity lower than the emissivity of said internal electrode; and wherein a clearance is formed between the heater and the internal electrode, the clearance being 0.1 mm or more.

2. An oxygen concentration detector according to claim 1, wherein said internal electrode consists of platinum black or ruthenium oxide.

3. An oxygen concentration detector according to claim 1, wherein a surface of said internal electrode facing said external electrode consists of a material having an emissivity higher than the emissivity of said external electrode.

4. An oxygen concentration detector according to claim 1, wherein said internal electrode material has an emissivity of more than 0.6.

5. An oxygen concentration detector comprising:

a sensor element including a solid electrolyte and external and internal electrodes provided on external and internal surfaces thereof, respectively;

a high-emissivity layer provided on a surface of said internal electrode; and a heater disposed adjacent to said high-emissivity layer to form a clearance therebetween, the clearance being 0.1 mm or more, wherein:

said internal electrode has an emissivity less than that of said high-emissivity layer; and said high-emissivity layer has an emissivity of 0.3 or more, and a porosity more than 10 percent.

6. An oxygen concentration detector according to claim 5, wherein said high-emissivity layer substantially consists of at least one material selected from a group consisting of alumina, titanium oxide, zirconium oxide, iron (III) oxide, nickel oxide, manganese oxide, copper oxide, cobalt oxide, chromium oxide, yttrium oxide, cordierite, silicon nitride, aluminum nitride, and silicon carbide.

7. An oxygen concentration detector according to claim 5, wherein said internal electrode is made of only noble metal.

8. An oxygen concentration detector according to claim 5, wherein said high-emissivity layer has a surface roughness of 1 $\mu$m or more.

9. An oxygen concentration detector according to claim 5, wherein said high-emissivity layer has a thickness of 5 $\mu$m or more.

10. An oxygen concentration detector according to claim 9, wherein the thickness of said high-emissivity layer is in a range of 10–20 $\mu$m.

11. An oxygen concentration detector comprising:

a sensor element including a solid electrolyte and external and internal electrodes provided on external and internal surfaces thereof, respectively;

a heater disposed within said sensor element adjacent to said internal electrode; and a high-emissivity layer provided on a surface of said heater to form a clearance between said high-emissivity layer and said internal electrode, wherein said high-emissivity layer has an emissivity of 0.6 or more, and a porosity more than a predetermined value.

12. An oxygen concentration detector according to claim 11, wherein said high-emissivity layer substantially consists of at least one material selected from a group consisting of iron (ill) oxide, nickel oxide, manganese oxide, copper oxide, cobalt oxide, chromium oxide, silicon nitride, aluminum nitride, and silicon carbide.

13. An oxygen concentration detector according to claim 11, wherein said internal electrode is made of only noble metal.

14. An oxygen concentration detector according to claim 11, wherein said high-emissivity layer has a surface roughness of 1 $\mu$m or more.

15. An oxygen concentration detector comprising:

a sensor element including a solid electrolyte and external and internal electrodes provided on external and internal surfaces thereof, respectively;

a heater disposed at an inner side of said internal electrode to be adjacent to said internal electrode;

a first high-emissivity layer provided on a surface of said heater; and a second high-emissivity layer provided on a surface of said internal electrode, wherein, said internal electrode has an emissivity less than that of said second high-emissivity layer;

each of said first high-emissivity layer and said second high-emissivity layer has an emissivity of 0.3 or more, and a porosity more than a predetermined value; and said first high-emissivity layer is separated from said second high-emissivity layer to form a clearance therebetween, the clearance being 0.1 mm or more.

16. An oxygen concentration detector comprising:

a sensor element including a solid electrolyte and external and internal electrodes provided on external and internal surfaces thereof, respectively; and a heater disposed adjacent to said internal electrode to form a clearance therebetween, the clearance being 0.1 mm or more;

wherein said heater has an emissivity of 0.6 or more, wherein said heater has a polygonal cross-section.

17. An oxygen concentration detector according to claim 16, wherein said heater consists of at least one material selected from a group consisting of silicon nitride, aluminum nitride and silicon carbide.

18. An oxygen concentration detector according to claim 16, wherein said internal electrode is made of only noble metal.

19. An oxygen concentration detector according to claim 18, wherein each of said external and internal electrodes is made of only noble metal.

20. An oxygen concentration detector comprising:

a sensor element including a solid electrolyte and external and internal electrodes provided on external and internal surfaces thereof, respectively; and a heater disposed adjacent to said internal electrode;

a high-emissivity layer provided on a surface of said internal electrode to form a clearance between said heater and said high-emissivity layer, the clearance being 0.1 nun or more, wherein said high-emissivity layer has an emissivity higher than that of said external electrode, wherein said high-emissivity layer has a porosity of more than 10 percent.

* * * * *